(12) United States Patent
Lindsberg et al.

(10) Patent No.: US 8,163,734 B2
(45) Date of Patent: Apr. 24, 2012

(54) USE OF A MAST CELL ACTIVATION OR DEGRANULATION BLOCKING AGENT IN THE MANUFACTURE OF A MEDICAMENT FOR THE TREATMENT OF A PATIENT SUBJECTED TO THROMBOLYSES

(75) Inventors: Perttu J. Lindsberg, Helsinki (FI); Marja-Liisa Karjalainen-Lindsberg, Helsinki (FI); Turgut Tatlisumak, Helsinki (FI); Daniel Strbian, Helsinki (FI); Petri Kovanen, Espoo (FI)

(73) Assignees: Perttu J. Lindsberg, Helsinki (FI); Marja-Lissa Karjalainene-Lindsberg, Helsinki (FI); Turgut Tatlisumak, Helsinki (FI); Daniel Strbian, Espoo (FI); Petri Kovanen, Espoo (FI)

( * ) Notice: Subject to any disclaimer, the term of this patent is extended or adjusted under 35 U.S.C. 154(b) by 973 days.

(21) Appl. No.: 10/545,402

(22) PCT Filed: Feb. 13, 2004

(86) PCT No.: PCT/FI2004/000072
§ 371 (c)(1), (2), (4) Date: Feb. 6, 2006

(87) PCT Pub. No.: WO2004/071532
PCT Pub. Date: Aug. 26, 2004

(65) Prior Publication Data
US 2006/0210551 A1   Sep. 21, 2006

(51) Int. Cl.
*A61K 38/48* (2006.01)
*A61K 31/55* (2006.01)
*A61K 31/495* (2006.01)
*A61K 31/353* (2006.01)

(52) U.S. Cl. .............. 514/217.05; 514/255.04; 514/456; 424/94.64

(58) Field of Classification Search .................... None
See application file for complete search history.

(56) References Cited

U.S. PATENT DOCUMENTS

| | | | |
|---|---|---|---|
| 4,447,449 A | | 5/1984 | Marshall |
| 4,584,315 A | * | 4/1986 | Marshall ................ 514/456 |
| 5,808,109 A | * | 9/1998 | Sindelar et al. ............ 549/345 |
| 5,952,296 A | | 9/1999 | Bigazzi |
| 2002/0122796 A1 | * | 9/2002 | Cummings et al. ........ 424/130.1 |

FOREIGN PATENT DOCUMENTS

| | | |
|---|---|---|
| EP | 0308802 A2 | 3/1989 |
| EP | 0448029 A3 | 9/1991 |
| EP | 1008348 A1 | 6/2000 |
| WO | WO 93/12773 A1 | 7/1993 |
| WO | WO 01/62241 A1 | 8/2001 |

OTHER PUBLICATIONS

T.S.C. Orr & J.S.G. Cox, "Disodium Cromoglycate, an Inhibitor of Mast Cell Degranulation and Histamine Release induced Phospholipase A" Nature, 1969, 223, pp. 197-198.*
M. Nishibori & K. Saeki, "Disodium Cromoglycate Inhibition of Substance P-Induced Secretion is Calcium Dependent" Japan. J. Pharmacol., 1983, 33, pp. 1255-1261.*
J.M. Smith, "Increased Dosage of Disodium Cromoglycate," Brit. Med. J., 1973, pp. 303-304.*
Vural et al., "Effects of mast cell membrane stabilizing agents in a rat lung ischemia-reperfusion model", Annals of Thoracic Sur., 2000, 69(1), pp. 228-232.*
Pamela Esposito, et al., "Acute stress increases permeability of the blood-brain-barrier through activation of brain mast cells", Brain Research, vol. 888, (2001), pp. 117-127.
Kerem M. Vural, et al., "Effects of mast cell membrane stabilizing agents in a rat lung ischemiareperfusion model", The Annals of Thoracic Surgery, Jan. 2000, vol. 69, Issue 1, pp. 228-232.
STN International, File MEDLINE, MEDLINE accession No. 95066883, Zhang Q Z et al., "Effects of cyproheptadine on TXB2 and 6-keto-PGF 1 alpha plasma levels in rabbits with hemorrhagic shock", Zhongguo yao li xue bao = Acta pharmacologica Sinica, (May 1194), 15 (3) 226-8.
National Library of Medicine (NLM), File MEDLINE; MEDLINE accession No. 7976381, Xin H B et al., "Protective effects of injury in isolated rat hearts", & Zhongguo yao li xue bao = Acta pharmacologica Sinica, CHINE, May 1994, ISSN 0253-9756, vol. 15, No. 3 pp. 253-257.
Lindsberg et al, *Duodecim*, 113(181:1765 (1997).
Dowdall, J. F.. et al., "Biological role and clinical implications of mast cells in surgery" Jul. 2002, vol. 132, No. 1, pp. 1-4.
Valent, P. et al., "New Aspects in Thrombosis Research: Possible Role of Mast Cells as Profibrinolytic and Antithrombotic Cells" Thromb Haemost 2002; 87, p. 786-790.

* cited by examiner

*Primary Examiner* — James D Anderson
*Assistant Examiner* — Bong-Sook Baek
(74) *Attorney, Agent, or Firm* — Sughrue Mion, PLLC

(57) ABSTRACT

The invention concerns the use of a mast cell activation- or degranulation-blocking agent in the manufacture of a medicament for preventing and treating cerebral complications caused by thrombolytic treatment. The invention also relates to treatment of patients suffering from cerebral complications associated with thrombolysis. Further, the invention provides thrombolytic compositions comprising a mast cell degranulation-blocking and/or mast cell activation-blocking agent present in a therapeutically effective amount to prevent or reduce any cerebral complications caused by the active thrombolytic component.

5 Claims, 5 Drawing Sheets

USE OF A MAST CELL ACTIVATION OR DEGRANULATION BLOCKING AGENT IN THE MANUFACTURE OF A MEDICAMENT FOR THE TREATMENT OF A PATIENT SUBJECTED TO THROMBOLYSES

CROSS-REFERENCE TO RELATED APPLICATIONS

This application is a 371 National Stage Entry of International Application No. PCT/FI2004/000072, filed Feb. 13, 2004, which claims priority to U.S. Patent Provisional Application No. 60/446,990, filed Feb. 13, 2003.

BACKGROUND OF THE INVENTION

1. Field of the Invention

The present invention relates to new therapeutic uses of known compounds. In particular, the invention relates to the use of mast cell activating- and degranulation-blocking agents for preventing and treating cerebral complications, such as reperfusion injury, inflammatory changes, brain edema, and similar damages occurring in connection with thrombolytic treatment.

2. Description of Related Art

Mast cells are present in the brain and located typically in perivascular spaces. They contain substantial amounts of pre-formed pro-inflammatory, vasoactive, anticoagulant and proteolytic substances. These substances are contained within numerous intracytoplasmic granules. They can synthesise a large number of additional substances. Generally, they protect parenchymal organs from exogenous, hazardous agents such as microbes and toxic or allergenic particles. The chymase found in the granules can lyse vascular basal membrane constituents such as fibronectin. Mast cells can influence the permeability of small cerebral vessels, regulate blood circulation and prime immunological responses. They can also mount an immediate host defence response by rapid degranulation, which can lead to hazardous anaphylactic and other systemic bodily reactions. Mast cells have been found in most parenchymal organs, including the brain and meninges as well as peritoneal organs such as the intestines.

Mast cells are targets of therapy to treat allergic reactions occurring in asthma or allergic conjunctivitis. Mast cells are also known to be activated and degranulated during mechanical manipulations in the skin as well as trauma to the various parts of the body, and parenchymal organs, but this has not been a basis for any therapeutic methods or modifications of surgical procedures. There are currently no approved medical treatments, which would depend on specific modulation of the mast cell function in the brain, but there have been speculations that they participate pathophysiologic events in migraine, multiple sclerosis, neuroendocrine reactions such as psychological stress reactions and Wernicke's encephalopathy, a rare brain disease caused by malnutritional state. In the treatment and various clinical investigations of cerebrovascular disease such as ischemic and hemorrhagic stroke, brain trauma, brain tumors or increased intracranial pressure, mast cells are not considered as participants of the diseases or targets of therapeutic interventions.

Thrombolytic therapy has been the culprit of acute myocardial infarction and massive pulmonary embolism for a decade. It is given often already by the emergency dispatch medical personnel outside the hospital. It is also used in acute occlusions of peripheral arteries to prevent limb necrosis. Thrombolytic therapy with alteplase (recombinant tissue plasminogen activator, r-TPA) has recently been approved also for acute ischemic stroke in North America and Europe. Stroke thrombolysis necessitates the rapid transport of patients into the hospital to receive computed tomography to rule out a brain hemorrhage.

r-TPA is a serine protease leading to plasmin formation, which dissolves fibrin fibres, a major constituent of arterial thrombi. Although the action of r-TPA is considered relatively specific, and the specificity of thrombolytic substances is under constant research and pharmacological development, thrombolysis is associated with hemorrhagic complications such as gastrointestinal bleeding and hematomas of the parenchymal organs. Those occurring in the brain are among the most dreaded and can be fatal. In acute myocardial infarctions, the rate of intracranial bleeding is 0.5-1.0%, but in acute ischemic stroke the frequency of parenchymal hematomas is 6-11%. An equal additional amount of patients undergo hemorrhagic transformation of the ischemic stroke, which, however, can occur also in patients who do not receive thrombolysis. When treating ischemic stroke patients with thrombolysis, the single most feared complication and factor to preclude treatment is the possibility to cause serious intracranial hemorrhage with the treatment. Furthermore, it can be associated with enhanced reperfusion injury and brain edema. If these safety issues would be solved, a much larger fraction of stroke patients today would receive thrombolytic therapy.

Today, there are no substances in clinical use to reduce the rates of hemorrhagic complications in thrombolysis. To prevent hemorrhages, arterial blood pressure is controlled and kept under 185/110 mmHg. However, perithrombolytic administration of antihypertensive compounds has been associated with poor functional prognosis, which may relate to reduced cerebral perfusion. Patients who might have increased tendency to bleed, such as those with reduced hemostasis, malignancies, anticoagulant therapy or recent biopsies or operations, are generally not treated with thrombolytics to prevent hemorrhagic complications.

For the reasons, there is a great need for alternative or additional methods for preventing or treating brain edema and similar cerebral damages caused by thrombolytic treatment.

SUMMARY OF THE INVENTION

It is an object of the present invention to provide a new use of mast cell degranulation-blocking and/or mast cell activation-blocking agents.

It is another object of the present invention to provide a novel method for treating and protecting patients subjected to thrombolytic treatment from cerebral complications, such as brain edema, and for specifically protecting the brain-blood barrier.

It is a third object of the present invention to provide novel thrombolytic compositions.

These and other objects, together with the advantages thereof over the known therapeutic uses, which shall become apparent from specification, which follows, are accomplished by the invention as hereinafter described and claimed.

In connection with the present invention, it has been observed that mast cells are present in the brain tissue, surrounding small cerebral vessels in perivascular spaces, and increase in number, and commonly degranulate, during and following induced cerebral ischemia. They colocalize with perivascular edema formation, early leukocyte emigration from the blood circulation as well as erythrocyte extravasation. It is therefore believed that the initial response of stationary mast cells is in part causing later events leading to florid blood-brain barrier damage and the entry of circulating inflammatory cells, which can aggravate the brain injury and disrupt the blood-brain barrier to larger particles, such as erythrocytes.

The present inventors have discovered that preischemic administration of mast cell stabilizer cromoglycate, which prevents mast cell degranulation, into the cerebral ventricles, prevented 39% of the brain edema observed already 3 hours after 60 minutes of middle cerebral artery occlusion in the rat. Furthermore, in connection with the present invention, the Inventors observed that a mast cell degranulating agent, compound 48/80, administered before reperfusion aggravated the brain edema by 89%. Furthermore, the Inventors observed that cerebral extravasation of plasma constituents was similarly influenced by the same treatments in the ischemic brain area. Therefore, mast cell degranulation seems to participate in ischemic blood-brain barrier damage, and could underlie in part the extravasation of blood cells and hemorrhagic transformation.

The inventors have also found that rat peritoneal mast cells ex vivo are degranulated by alteplase solution. In the rat brains, degranulation of cells consistent with mast cell morphology during a 90 minute ischemic period occurs in a subtotal manner up to 50%, and can be significantly increased both in the ischemic (up to 70%) and non-ischemic hemispheres (up to 60%) by systemically administered r-TPA infusion 5 minutes before reperfusion. This associated with substantial hemorrhage formation in the same rat brains. Furthermore, r-TPA infusion led to substantial neutrophil emigration into the brain parenchyma and adhesion within the cerebral microvessels, and the total number of neutrophils found in the tissue was up to 5-fold increased in the non-infarcted hemisphere and up to 3-fold increased in the ischemic hemisphere. The presence of neutrophils was positively correlated with the degranulation state of the cells consistent with mast cell morphology in the same brains. It is therefore conceived that mast cell-derived chemokines participate in building the chemotactic gradient up which neutrophils are migrating into the tissue. This can also increase the likelihood of florid erythrocyte extravasation leading to hemorrhagic tissue changes.

By using substances, such as cromoglycate, whose pharmacological effect consists essentially exclusively of affecting the degranulation or activation of mast cells or inhibiting the main granula constituents of cerebral mast cells, it is possible to protect and treat complications, such as brain edema and hemorrhagic brain insults, caused by the breaking down of the brain-blood barrier during thrombolysis. For the purpose of the present invention, cromoglycate and the similar compounds, such as any 2-carboxylatomchromon-5'-yl-2-hydroxypropane derivatives, nedocromil and tranilast, are considered to be agents, which specifically prevent or reduce mast cell degranulation or activation, in the sense that they do not have other major tissue activity except for that exhibited through their mast cell degranulation or activation blocking mechanism. Similarly, as will be discussed in more detail below, inhibitors of the c-kit receptors on mast cells as well as chymase and procollagenase activators can be used in the present invention.

The present invention provides new thrombolytic compositions, which contain a therapeutically effective amount of a mast cell degranulation-blocking and/or mast cell activation-blocking agent, to prevent cerebral complications, such as brain edema or hemorrhagic brain insults, in a patient during or after thrombolysis.

The invention also comprises the use of a mast cell degranulation-blocking and/or mast cell activation-blocking agent in the manufacture of a medicament for preventing or reducing mast cell degranulation in a patient subjected to thrombolysis.

In the following, the term "mast cell degranulation-blocking agent" will be used interchangeably with "mast cell degranulation-blocking and/or mast cell activation-blocking agent" to designate an agent having either or both of the two activities: mast cell degranulation blocking and mast cell activation blocking. Preferably the activity is, as discussed above, specific. Within the above definition are also included compounds acting primarily on c-kit receptor responsible of mast cell maturation and activation, and its intracellular signaling pathway.

The invention further provides efficient precaution against cerebral edematous change in thrombolytic conditions conducive to cerebral ischemia. The treatments according to the invention involve the administration of a therapeutically effective amount of a mast cell degranulation-blocking and/or mast cell activation-blocking agent By the present invention, significant reductions in serious hemorrhagic, especially cerebral complications, in thrombolytic treatments, can be reached. The reduction of ischemic edema is up to 40% compared to control can be obtained (this figure is based on the animal experiments described in detail below). The finding was surprising, since it has long been held that the immediate phase of brain edema is caused by cytotoxic mechanism leading to a shift of extracellular fluid, not intravascular fluid, into the cerebral cellular compartment.

DETAILED DESCRIPTION OF THE INVENTION

Figure 1:
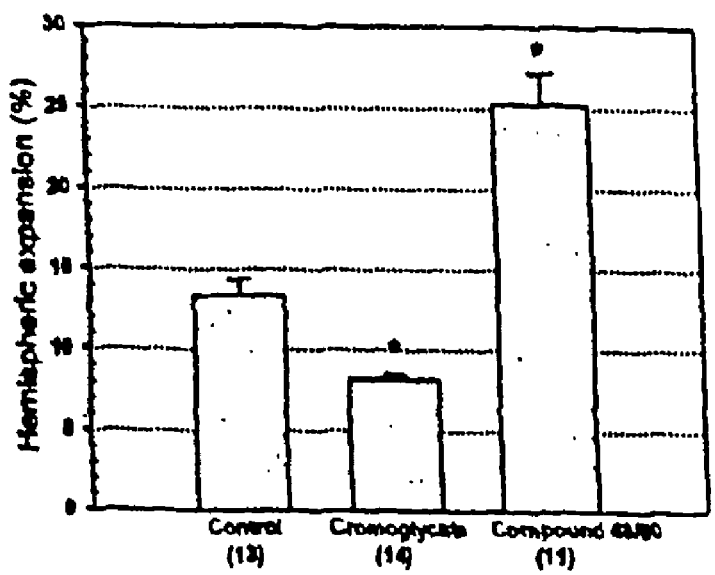
FIG. 1 is a bar chart showing the percentual hemispheric expansion caused by focal cerebral ischemia in rats after pretreatment with two different substances in comparison to control.

Cerebral mast cells degranulate to some extent during ischemic stroke and their degranulation is further increased by r-TPA treatment. Mast cell granules contain heparin, and are the only cell type of the body capable of heparin synthesis. Should there occur subtle breaches of blood-brain barrier to allow red blood cell extravasation, the heparin released by mast cells may prevent the formation of fibrin fibres for the platelets to attach and form a plug preventing further extravasation. Furthermore, mast cells release chymase, which is a potent proteolytic substance and lyses the fibronectin of the vascular basal membrane.

Plasmin can also activate neutrophil-derived metalloproteinases that lyse collagen. These mechanisms may give rise to lysis of two of the three major components (laminin, collagen, fibronectin) of the vascular basement membrane. These events can initiate local bleedings and even solid parenchymal hematomas, if this phenomenon occurs in the vicinity of small arterial vessels such as the penetrating arteries in the basal ganglia and thalamus. These are well-known predilection areas of the presence of cerebral mast cells as well as spontaneous cerebral bleedings.

Although many of the triggering factors for mast cell degranulation have been documented, the major trigger in cerebral ischemia remains unknown. One mechanism may relate to complement protein activation, formation of anaphylatoxins C3a and C5a, which are among the most potent activators of mast cells. The present inventors have previously demonstrated that terminal ischemic and hemorrhagic brain insults produce activation of the terminal complement pathway, which involves the synthesis of anaphylatoxins. Interestingly, it was demonstrated that even in vitro mixing of ex vivo human plasma and cerebrospinal fluid led to complement activation. Therefore, even temporary and subtle initial breaches of the blood-brain barrier early during ischemia might produce C3a and C5a and trigger mast cell degranulation and more florid BBB damage and eventual brain edema. Other mechanisms could include production of cytokines such as interleukins of tumor necrosis factor-$\alpha$.

Since r-TPA increased the mast cell degranulation both in vitro and in vivo, inhibitors of mast cell degranulation and activation might prove effective in preventing a fraction of the feared hemorrhagic complications of thrombolytic treatment, especially in the brain. Furthermore, mast cell stabilizing therapies might attenuate the reperfusion injury caused by neutrophils infiltrating the brain parenchyma. This is a common sequel in ischemic stroke even in the absence of thrombolysis. Furthermore, application of these therapies might help to increase the fraction of patients that today can be considered eligible for thrombolytic therapy.

Practical applications of the present invention include:
I. Prevention of Serious Hemorrhagic, Especially Cerebral Complications, in the Thrombolytic Treatment
  Typical applications include
  1) acute ischemic stroke
  2) acute myocardial infarction
  3) massive pulmonary embolism
  4) occlusion of peripheral arteries
  5) thrombolysis of intracerebroventricular haematoma
II. Prevention of Reperfusion Injury, Inflammatory Changes and Brain Edema Associated with Recanalization of Cerebral Artery Occurring Spontaneously or after Thrombolysis According to the invention, a mast cell degranulation-blocking or mast cell activation-blocking agent is employed. The agent may have either or both of these activities. The aim is in particular to stabilize the mast cells by, e.g. preventing degranulation of the cells and the release of substances contain in the granulas. Generally speaking, activation of mast cells is to be avoided within the scope of the present invention.

The mast cell degranulation-blocking or mast cell activation-blocking agent can be administered separately from the thrombolytically active component. Preferably, it is however incorporated into the thrombolytic composition.

If administered separately, the mast cell degranulation-blocking or mast cell activation-blocking agent should preferably be administered before, preferably at least 5 minutes, in particular at least 10 minutes before the patient is subjected to thrombolysis.

If incorporated into the thrombolytical composition, the agent is present in a therapeutically effective amount to prevent or reduce any cerebral complications, such as brain edema, in a patient subjected to thrombolytic treatment.

The mast cell degranulation-blocking (including mast cell activation-blocking) agent is, according to the invention, preferably selected from the group of 2-carboxylatochromon-5'-yl-2-hydroxypropanederivatives and histamine-1 receptor antagonists. Examples of mast cell degranulation-blocking agents of the first group are bis(acetoxymethyl) cromoglycate, disodium cromoglycate and nedocromil. Further compounds exhibiting selective mast cell degranulation/activation blocking effect include tranilast, and compounds acting primarily on (inhibiting) the c-kit receptor responsible of mast cell maturation and activation, such as imatinibe (e.g. in the form of its mesylate salt).

Examples of the histamine-1 inhibitors are: azatadine, azelastine, burfroline, cetirizine, cyproheptadine, doxantrozole, etodroxizine, forskolin, hydroxyzine, ketotifen, oxatomide, pizotifen, proxicroril, N,N'-substituted piperazines and terfenadine.

Further examples include flavonoids, which inhibit mast cell secretion and proliferation. These are exemplified by quercetin optionally in combination with the proteoglycan chondroitin sulphate. Histamine-2 receptor antagonists, such as cimetidine, optionally combined with e.g. hydroxyzine, along with indolinone derivatives, and IPD-1151T are other examples.

The present invention also provides for prevention of mast cell-induced blood-brain barrier damage by inhibition of the main granule constituents of cerebral mast cells, which lyse basal lamina proteins, such as chymase, and procollagenase activators. Thus, substances specifically inhibiting chymase and procollagenase activators, such as TIMP (tissue inhibitors of metalloproteinase 1) are included, in particular substances capable of penetrating the blood-brain barrier. Even compounds capable selectively of inhibiting the histamine released from mast cells should be considered.

The mast cell degranulation-blocking and/or mast cell activation-blocking agent is administered in a therapeutically efficient amount. Typically, that amount is about 0.05 to 100 milligrams per kilogram body weight of the patient.

The present invention provides for new thrombolytic compositions, which contain a component preventing or alleviating cerebral complications caused by the active components. The thrombolytically active component is typically selected from the group of alteplase, tenecteplase, reteplase, and streptochinase. As examples of commercial compositions which can be complemented with the agent, the following can be mentioned: Actilyse (supplier Boehringer Ingelheim), Metalyse (supplier Boehringer Ingelheim), Rapilysin (supplier: Roche) and Streptase (supplier: Aventis Behring). Such a compositions are, according to the invention, complemented with a suitable amount of a mast cell degranulation-blocking and/or mast cell activation-blocking agent. The amount is generally 0.01 to 100 mg/l. The thrombolytic compositions are formulated for parenteral administration.

When separately administered, the compounds employed in the methods of the present invention may be administered by any means that results in the contact of the active agent with the agent's site of action in the body of a patient. The compounds may be administered by any conventional means available for use in conjunction with pharmaceuticals, either as individual therapeutic agents or in a combination of therapeutic agents. For example, they may be administered as the sole active agent in a pharmaceutical composition, or they can be used in combination with other therapeutically active ingredients.

The compounds may be combined with a pharmaceutical carrier selected on the basis of the chosen route of administration and standard pharmaceutical practice as described, for example, in Remington's Pharmaceutical Sciences (Mack Pub. Co., Easton, Pa., 1980), the disclosures of which are hereby incorporated herein by reference, in their entireties.

Compounds of the present invention can be administered to a mammalian host in a variety of forms adapted to the chosen route of administration, e.g., orally or parenterally. Parenteral administration in this respect includes administration by the following routes: intravenous, intramuscular, subcutaneous, rectal, intraocular, intrasynovial, transepithelial including transdermal, ophthalmic, sublingual and buccal; topically including ophthalmic, dermal, ocular, rectal, and nasal inhalation via insufflation aerosol. The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should preferably contain at least about 0.1% of active compound. The percentage of the compositions and preparations may, of course, be varied and may conveniently be, for example, from about 2 to about 6% of the weight of the unit. The amount of active compound in such therapeutically useful compositions is preferably such that a suitable dosage will be obtained. Preferred compositions or preparations according to the present invention may be prepared so that an oral dosage unit form contains from about 0.1 to about 1000 mg of active compound, and all combinations and subcombinations of ranges and specific amounts therein.

The tablets, troches, pills, capsules and the like may also contain one or more of the following: a binder, such as gum tragacanth, acacia, corn starch or gelatin; an excipient, such as dicalcium phosphate; a disintegrating agent, such as corn starch, potato starch, alginic acid and the like; a lubricant, such as magnesium stearate; a sweetening agent such as sucrose, lactose or saccharin; or a flavoring agent, such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring, such as cherry or orange flavor. Of course, any material used in preparing any dosage unit form is preferably pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or a pharmacologically acceptable salt can be prepared in water suitably mixed with a surfactant, such as hydroxypropylcellulose. A dispersion can also be prepared in glycerol, liquid polyethylene glycols and mixtures thereof and in oils. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions may be achieved by the use of agents delaying absorption, for example, aluminum monostearate and gelatin.

Sterile injectable solutions may be prepared by incorporating the active compound in the required amount, in the appropriate solvent, with various of the other ingredients enumerated above, as required, followed by filtered sterilization. Generally, dispersions may be prepared by incorporating the sterilized active ingredient into a sterile vehicle that contains the basic dispersion medium and the required other ingredients from those enumerated above. In the case of sterile powders for the preparation of sterile injectable solutions, the preferred methods of preparation may include vacuum drying and the freeze drying technique, which yield a powder of the active ingredient, plus any additional desired ingredient from the previously sterile-filtered solution thereof.

The therapeutic compounds of this invention may be administered to a patient alone or in combination with a pharmaceutically acceptable carrier. As noted above, the relative proportions of active ingredient and carrier may be determined, for example, by the solubility and chemical nature of the compound, chosen route of administration and standard pharmaceutical practice.

The dosage of the compounds of the present invention that will be most suitable will vary with the form of administration, the particular compound chosen and the physiological characteristics of the particular patient under treatment.

In particular, adminstration can be carried out parenterally, for example by i.v., i.c.v. (intracerebroventricularly) and i.m. administration. Parenteral compositions usually contain a buffering agent and, optionally, a stabilizing agent.

When necessary, in order to promote penetration of the blood-brain-barrier, the active compounds can be administered by using various known strategies for gaining drug access to the brain. These include the transcellular lipophilic pathway, which allows small, lipophilic compounds to cross the blood-brain barrier. A second pathway is "receptor-mediated endocytosis. Further, as known in the art, some experimental work has shown that a monoclonal antibody for the transferrin receptor, coupled with brain-derived neurotrophin factor, which is neuroprotective but cannot cross the barrier itself, can both cross the barrier and exert neuroprotective effects. Endothelial cells of the blood-brain barrier also express a number of transport proteins, including transporters for glucose, amino acids, nucleosides, and other compounds. Thus, to focus on the latter strategy, the compounds can be designed such that they gain access to the brain by going through these transport processes. It is, however, also possible to block these processes, in that way bolstering brain levels of endogenous permeant.

For the sake of completeness, it should be pointed out that the compounds employed in the uses and methods of the present invention may exist in prodrug form. As used herein, the term "prodrug" is intended to include any covalently bonded carriers which release the active parent drug or other formulas or compounds employed in the methods of the present invention in vivo when such prodrug is administered to a mammalian subject. Since prodrugs are known to enhance numerous desirable qualities of pharmaceuticals (e.g., solubility, bioavailability, manufacturing, etc.), the compounds employed in the present methods may, if desired, be delivered in prodrug form. Thus, the present invention contemplates methods of delivering prodrugs. Prodrugs of the compounds employed in the present invention may be prepared by modifying functional groups present in the compound in such a way that the modifications are cleaved, either in routine manipulation or in vivo, to the parent compound.

Accordingly, prodrugs include, for example, compounds described herein in which a hydroxy, thiol, amino, or carboxy group is bonded to any group that, when the prodrug is administered to a mammalian subject, cleaves to form a free hydroxyl, thiol, free amino, or carboxylic acid, respectively. Examples include, but are not limited to, acetoxyalkyls, acetate, formate and benzoate derivatives of alcohol, thiol, and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

To make drug delivery route more practical especially in the clinical setting, rat MCAO model can be used as described in detail in this application by replacing i.c.v. drug administration as the pretreatment before thrombolysis with intravenous (i.v.) drug administration of an alternative mast cell degranulation-blocking and/or mast cell activation-blocking agent, which possess the capacity to penetrate through blood-brain barrier more effectively than sodium cromoglycate.

Next, the invention will be illustrated with examples:

EXAMPLE 1

Methods

The suture filament model was used to induce focal cerebral ischemia for 60 min in rats. Reperfusion was allowed for 3 h, at which point the rats were killed, cardioperfused and their brains were dissected into coronal sections. Evans Blue-albumin (2%, 0.3 ml/100 g) a fluorescent dye, was injected i.v. 20 min before termination to monitor BBB (blood brain barrier) permeability. TTC (2,3,5-triphenyltetrazolium chloride, 2%) staining was used to quantitate the infarct volumes. The volumetric expansion of the ischemic hemisphere was quantitated with computerized planimetry. Rats were assigned in three pharmacological treatments: mast cell stabilizer disodium cromoglycate 750 ug in 10 ul i.c.v. (does not easily cross BBB) (n=14) or control (10 ul saline i.c.v.) (n=13) 5 min prior to ischemia, and a mast cell degranulation agent, compound 48/80 (n=11) administered (0.025 mg i.v.) 3 min prior to reperfusion. The Evans Blue extravasation was analysed using fluorescence microscopy and computerized image analysis-based quantitation of the fluorescent pixels in five random regions of interest.

Figure 2:
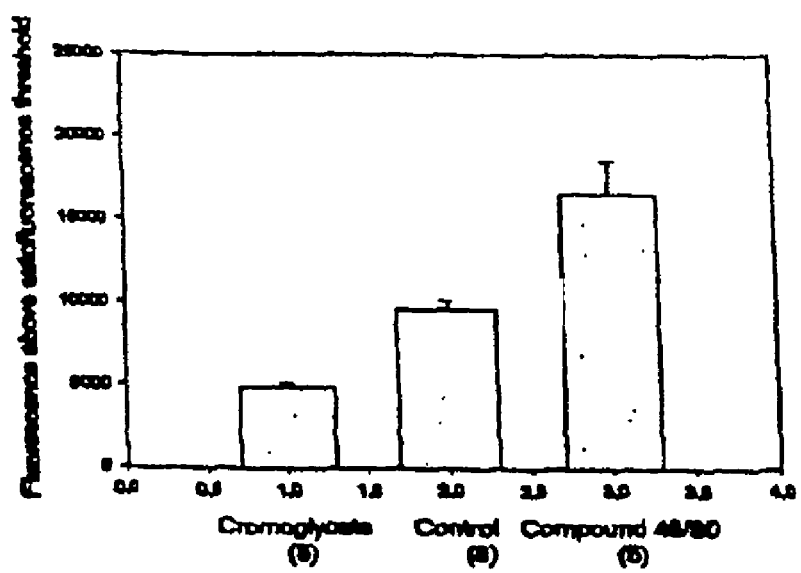
FIG. 2 is a bar chart showing the fluorescence above autofluorescence threshold for the same samples as in FIG. 1.

Results:

The volumetric hemispheric expansion caused by ischemia was highly significantly influenced by pharmacologic modulation of mast cell degranulation (Kruskal-Wallis ANOVA $p<0.001$, FIG. 1), as well as the mean number of fluorescent pixels indicating rates of extravasation ($p<0.001$, FIG. 2). Corrected infarct volumes were not influenced by the treatments: control 189±31, cromoglycate 252±41, compound 48/80 193±24 mm$^3$, $p=0.33$.

The results confirm the observations discussed above: inhibition of mast cell degranulation by intraventricular administration of cromoglycate led to a 39% reduction of the acute-phase ischemic edema.

EXAMPLE 2

Figure 3:
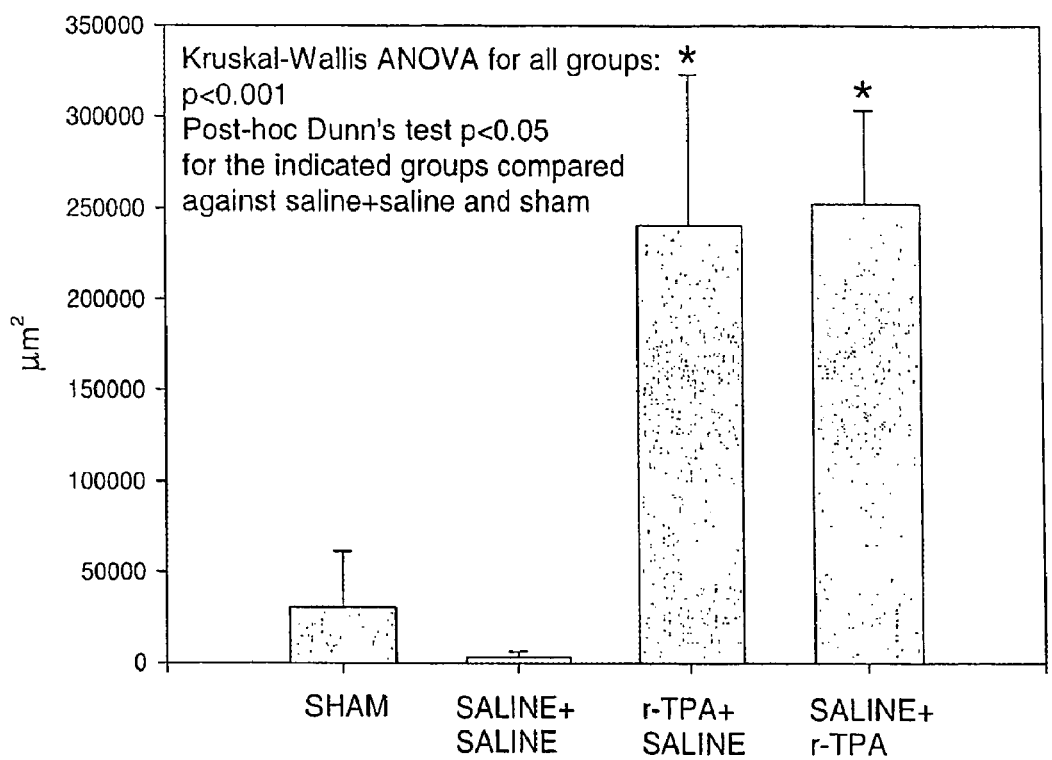
FIGS. 3 to 6 are further bar charts showing the results of Examples 2 and 3.

Rats were given 10 mg/kg of r-TPA, which is considered equivalent to the typical dose given to humans in thrombolysis in stroke and myocardial infarction. Two timings of r-TPA were used to investigate in rat brain the hemorrhagic conversion of infarction, the single most serious complication and hazard in clinical thrombolytic therapy. The group termed r-TPA+saline received 1-hour infusiuon of r-TPA starting 5 minutes (10% as bolus) prior to reperfusion after 90 min of middle cerebral artery occlusion (MCAO), whereas the group saline+r-TPA received r-TPA starting 1 hour after the reperfusion after 90 min of MCAO. Both timings resulted in significant hemorrhage formation, as compared to sham operated or saline-treated controls. Brains were dissected at 4.5 hours after reperfusion. Areas of hemorrhage were measured by microscopical image analysis on six histological sections cut through the hemispheres and added together (cf. FIG. 3)

Figure 4:
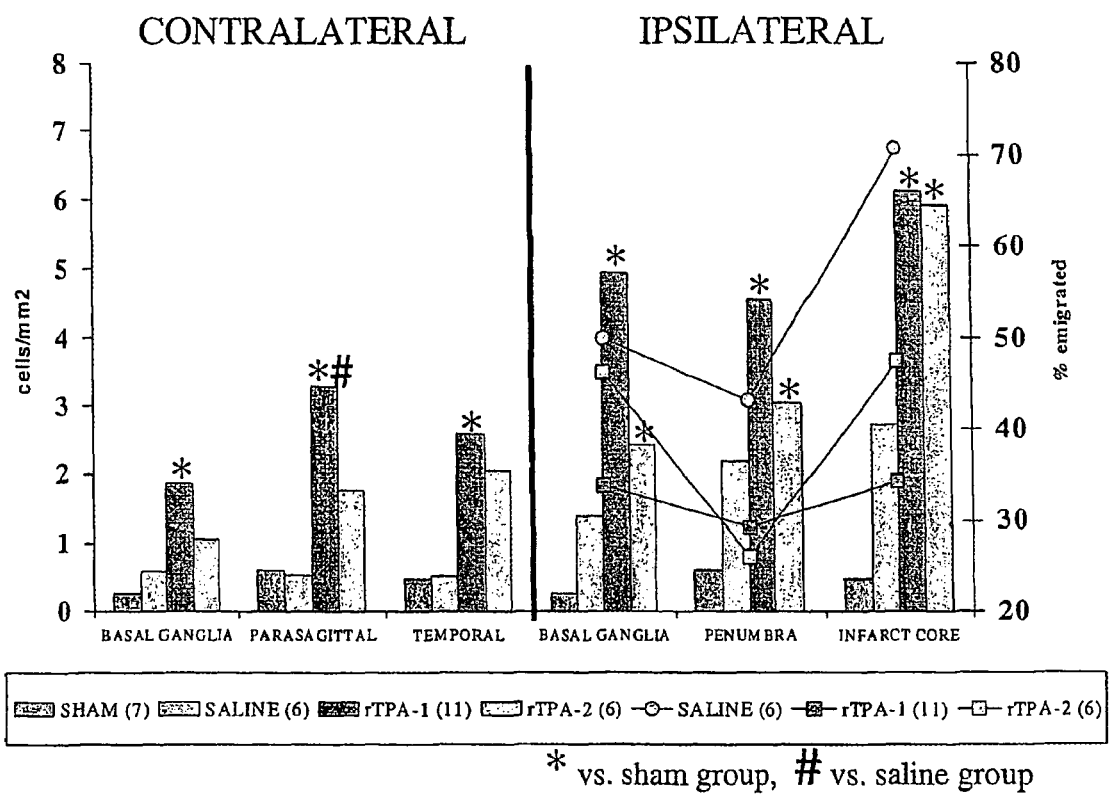

The polymorphonuclear leukocytes (neutrophils, shown in bars, left Y-axis, of FIG. 4) were calculated on the section encompassing the basal ganglia, infarct core and penumbra. While both groups that received r-TPA showed significantly increased neutrophil density compared to sham-operated rats, those which received only saline did not. r-TPA increased neutrophil counts even in the contralateral non-infarcted hemisphere. In the ipsilateral hemisphere, neutrophils appeared to be largely emigrated especially in the saline-treated rats (scatter plot, right Y-axis).

Figure 5:
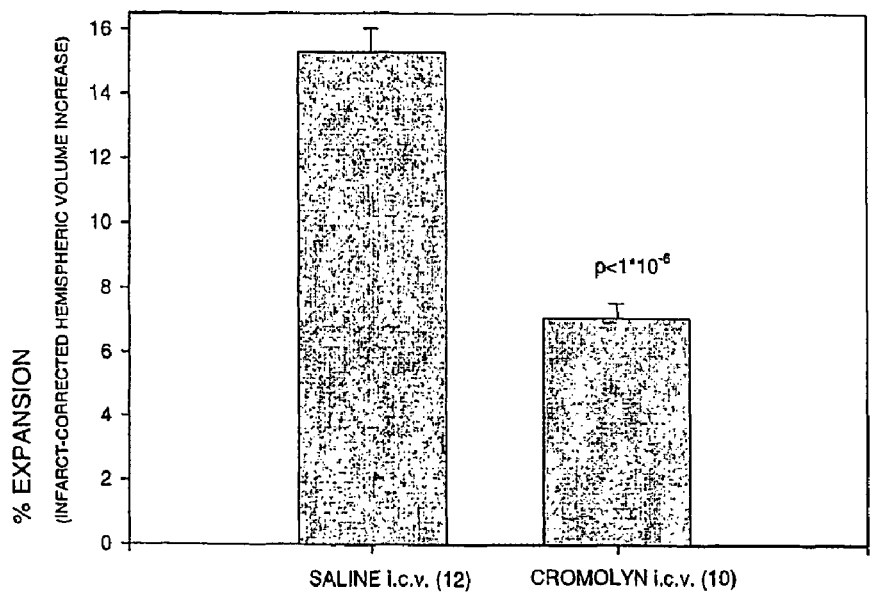
Figure 5:
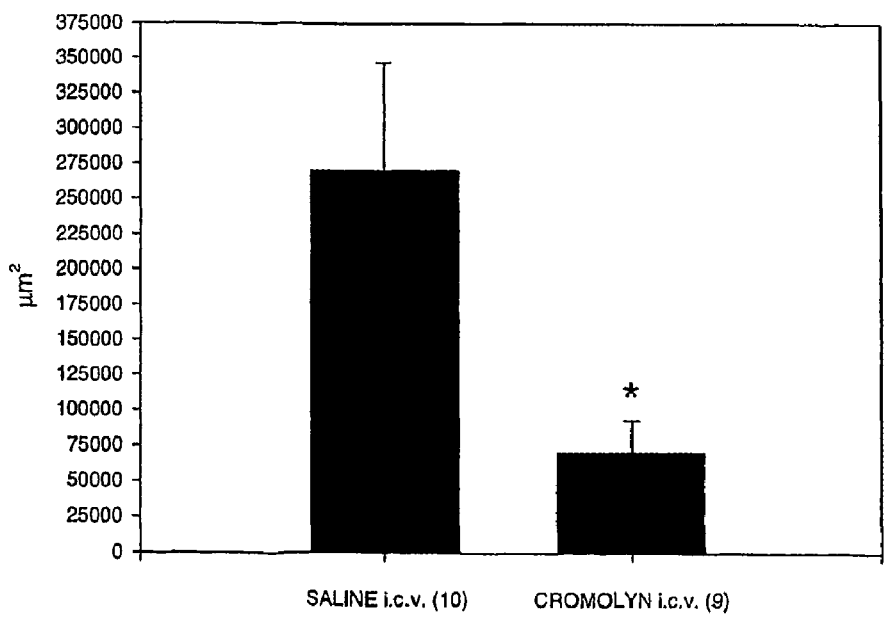

Rats were treated either with saline or cromoglycate i.c.v. and subjected to 90 min of MCAO. They were also treated with 10 mg/kg of r-TPA in a 1-hour infusion starting 2 min (10% as bolus) before reperfusion, a dose equivalent to that used clinically in thrombolysis of human stroke and myocardial infarction. Brains were dissected at 4.5 hours after reperfusion. The amount of brain edema was measured by quantitating the areas of hemispheres on histological sections with microscopical image analysis. The extent of hemispheric expansion (areas corrected by the size of infarctions) indicative of brain edema was found to be 54% reduced by cromoglycate (FIG. 5).

In the lower panel, the total area of hemorrhagic conversion was quantitated in six sections cut through the hemispheres. The i.c.v. cromoglycate treatment was found to decrease the area of hemorrhage significantly by 74%.

EXAMPLE 3

Additional data was derived from experiments using mast cell-deficient WsRc$^{Ws/Ws}$ rats carrying a defective gene for c-kit (ligand for stem cell factor [SCF]) required for mast cell differentiation) and their wild-type littermates. Animals were subjected to transient focal cerebral ischemia and treated with r-TPA as described above. In the mast cell deficient rats, the mean area of hemorrhage measured on the midline histological brain section was 142625:m$^2$ and 7100:m$^2$ in the wild-type littermates ($p<0.01$).

Figure 6:
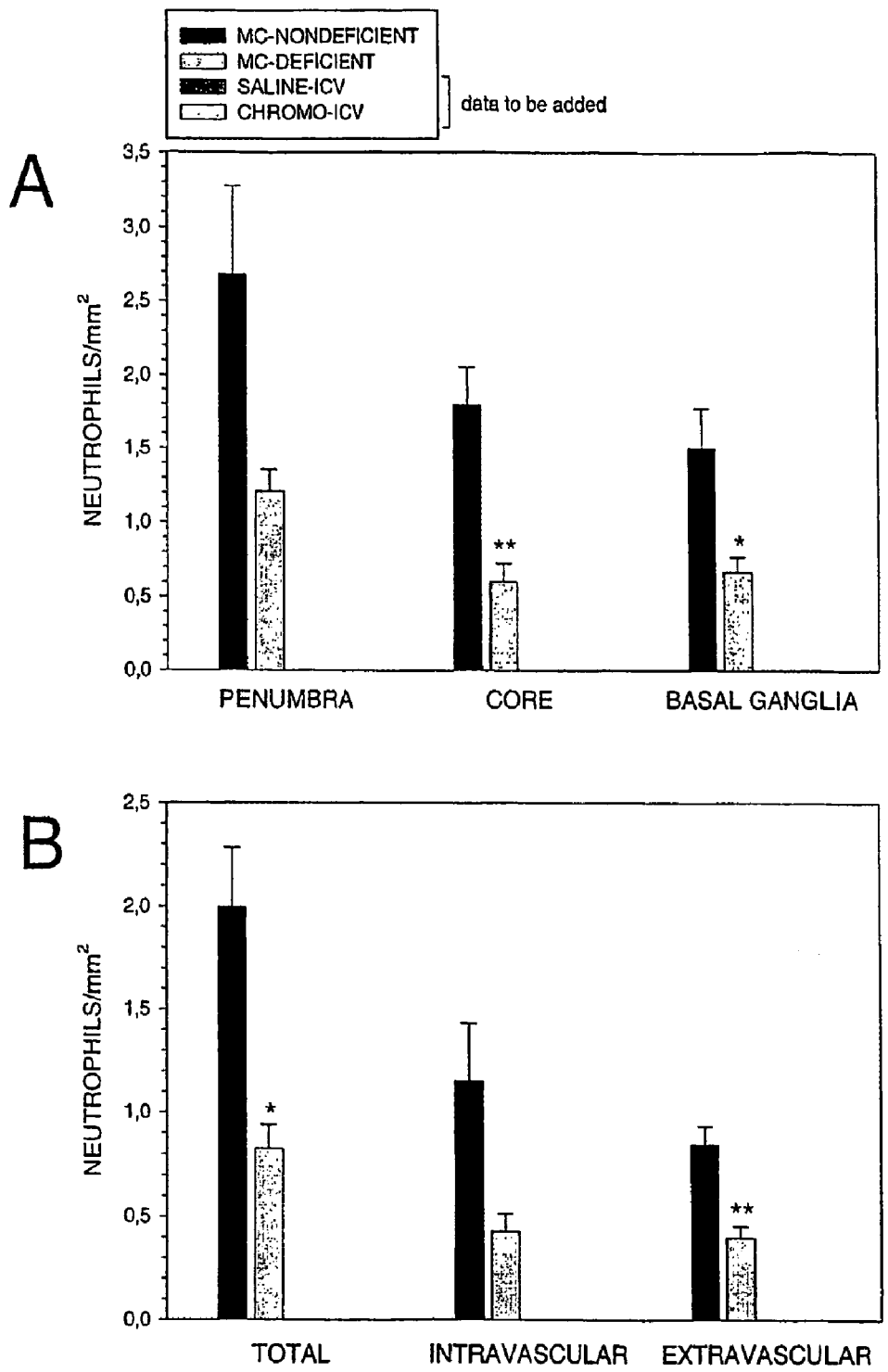

FIG. 6 shows the results obtained for MC-deficient gene manipulated rats and their non-manipulated littermates subjected to 90 min of MCAO and 4.5 hours of reperfusion. The density of neutrophils were counted in the tissue section encompassing basal ganglia, the infarct core and penumbra. The number of neutrophils was significantly reduced in the MC-deficient rats, especially in the infarct core and basal ganglia. In the lower panel it is indicated that the reduction in the pool of extravasated neutrophils was statistically most consistent. We perform additional analyses that will indicate the effect of cromoglycate therapy on the r-TPA-related neutrophil response, which is a component of reperfusion injury after recanalization of an occluded cerebral artery observed in FIG. 4.

The results presented indicate that interventions preventing mast cell degranulation (sodium cromoglycate as the model compound), as well as those influencing the function of c-kit receptor required for mast cell maturation, markedly reduce the hemorrhagic conversion when treating ischemic stroke with thrombolytic therapy. Furthermore, the resulting brain expansion is reduced by cromoglycate. Also the aggravation of inflammatory response, the neutrophil accumulation, is significantly reduced by sodium cromoglycate and c-kit knock-out. Therefore, mast cell inhibiting adjunct treatments would probably significantly improve the safety of thrombolytic therapies in man.

EXAMPLE 4

Thrombolysis with r-TPA of spontaneous intraventricular bleedings is an experimental treatment in humans, which accelerates the removal of detrimental blood clots from cerebral ventricles and subarachnoidal CSF spaces. However, the handicap of this treatment is that it more than doubles the rates of secondary brain hemorrhages in preliminary human experiments. This can cause fatal outcome and additional postoperative neurological disability. To eliminate this handicap, experiments can be performed in rats, which are subjected to intracerebroventricular hemorrhages induced by stereotactical infusion of autologous arterial blood. Comparisons are made of the rates of secondary cerebral hemorrhages in groups treated with a prolonged intraventricular r-TPA-infusion with and without prior and concomitant i.c.v. administration of sodium cromoglycate. The volume of hemorrhage and the rate of new intracerebral hemorrhages secondary to the r-TPA can be monitored by serial MRI (T2*sequence) and the total volume of hemorrhagic lesions in serial histological sections determined.

The invention claimed is:

1. A method for decreasing intracerebral hemorrhaging in a cerebral ischemia patient subjected to tissue plasminogen activator (TPA) treatment, comprising administering to said patient a therapeutically effective amount of a composition comprising a mast cell activation- or degranulation-blocking agent selected from the group consisting of bis(acetoxymethyl) cromoglycate, disodium cromoglycate, nedocromil and tranilast.

2. The method according to claim 1, wherein the mast cell activation- or degranulation-blocking agent is administered in an amount of about 0.05 to 100 milligrams per kilogram body weight of the patient.

3. The method according to claim 1, wherein said composition is formulated for parenteral administration.

4. The method according to claim 1, wherein said composition further comprises a thrombolytic agent.

5. The method according to claim 1, wherein the mast cell activation- or degranulation-blocking agent is disodium cromoglycate.

* * * * *